United States Patent [19]

Ushikubo et al.

[11] Patent Number: 5,231,214
[45] Date of Patent: Jul. 27, 1993

[54] PROCESS FOR PRODUCING NITRILES

[75] Inventors: Takashi Ushikubo, Yokohama; Kazunori Oshima, Machida; Tiaki Umezawa, Yokkaichi; Ken-ichi Kiyono, Machida, all of Japan

[73] Assignee: Mitsubishi Kasei Corporation, Tokyo, Japan

[21] Appl. No.: 880,687

[22] Filed: May 8, 1992

[30] Foreign Application Priority Data

May 9, 1991 [JP] Japan ................................. 3-104382

[51] Int. Cl.$^5$ ............................................. C07C 253/24
[52] U.S. Cl. ........................................ 558/319; 558/318
[58] Field of Search ........................................ 558/319

[56] References Cited

U.S. PATENT DOCUMENTS

| | | | |
|---|---|---|---|
| 3,649,562 | 3/1972 | Lane ................. | 558/319 X |
| 3,833,638 | 9/1974 | Knox et al. . | |
| 4,309,361 | 1/1982 | Suresh et al. ................. | 558/319 X |
| 4,814,478 | 3/1989 | Glaeser et at. .................. | 558/319 |
| 5,008,427 | 4/1991 | Brazdil, Jr. et al. ................. | 558/319 |
| 5,049,692 | 9/1991 | Hatano et al. ................. | 558/319 |

FOREIGN PATENT DOCUMENTS 0318295  5/1989  European Pat. Off. .
2-257    1/1990  Japan .

Primary Examiner—Joseph Paul Brust
Attorney, Agent, or Firm—Oblon, Spivak, McClelland, Maier & Neustadt

[57] ABSTRACT

A process for producing a nitrile, which comprises subjecting an alkane and ammonia in the gaseous state to catalytic oxidation in the presence of an oxide of the formula:

$$Mo_a V_b Te_c Nb_d X_x O_n \qquad (1)$$

wherein X is at least one element selected from the group consisting of Mg, Ca, Sr, Ba, Al, Ga, Tl, In, Ti, Zr, Hf, Ta, Cr, Mn, W, Fe, Ru, Co, Rh, Ni, Pd, Pt, Zn, Sn, Pb, As, Sb, Bi, La and Ce,
  when a=1,
  b=0.01 to 1.0,
  c=0.01 to 1.0,
  d=0 to 1.0, and
  x=0.0005 to 1.0, and n is a number such that the total valency of the metal elements is satisfied.

11 Claims, No Drawings

PROCESS FOR PRODUCING NITRILES

The present invention relates to a process for producing nitriles. More particularly, it relates to an improved method for producing nitriles by using alkanes or cyclohexane as starting material.

Nitriles such as acrylonitrile and methacrylonitrile have been industrially produced as important intermediates for the preparation of fibers, synthetic resins, synthetic rubbers and the like. The most popular method for producing such nitriles is to subject an olefin such as propylene or isobutene to a catalytic reaction with ammonia and oxygen in the presence of a catalyst in a gaseous phase at a high temperature.

On the other hand, in view of the price difference between propane and propylene or between isobutane and isobutene, an attention has been drawn to developing a method for producing acrylonitrile or methacrylonitrile by a so called ammooxidation reaction method wherein a lower alkane such as propane or isobutane is used as starting material, and it is catalytically reacted with ammonia and oxygen in a gaseous phase in the presence of a catalyst. For example, there have been reports on a Mo-Bi-P-O catalyst (Japanese Unexamined Patent Publication No. 16887/1973), a V-Sb-O catalyst (Japanese Unexamined Patent Publication No. 33783/1972, Japanese Examined Patent Publication No. 23016/1975 and Japanese Unexamined Patent Publication No. 268668/1989), a Sb-U-V-Ni-O catalyst (Japanese Examined Patent Publication No. 4371/1972), a Sb-Sn-O catalyst (Japanese Examined Patent Publication No. 28940/1975), a V-Sb-W-P-O catalyst (Japanese Unexamined Patent Publication No. 95439/1990), a catalyst obtained by mechanically mixing a V-Sb-W-O oxide and a Bi-Ce-Mo-W-O oxide (Japanese Unexamined Patent Publication No. 38051/1989). Further, the present inventors have reported on a Mo-V-Te-Nb-O catalyst (Japanese Unexamined Patent Publication No. 257/1990 and U.S. Pat. No. 5,049,692).

However, none of these methods is fully satisfactory in the yield of the intended nitriles. In order to improve the yield of nitriles, it has been proposed to add a small amount of an organic halide, an inorganic halide or a sulfur compound, or to add water to the reaction system. However, the former method has a problem of possible corrosion of the reaction apparatus, while the latter method has a problem of formation of by-products by side reactions or a problem of their treatment. Thus, each method has a practical problem for industrial application.

Further, methods using the conventional catalysts other than the Mo-V-Te-Nb-O catalyst reported by the present inventors, usually require a very high reaction temperature at a level of 500° C. or higher. Therefore, such methods are disadvantageous in terms of reactor material, production cost, etc.

The present inventors have conducted extensive researches on the method of producing nitriles by using an alkane as starting material. As a result, they have found it possible to produce a desired nitrile in better yield than conventional methods at a relatively low temperature of a level of from 400° to 450° C. without adding a halide or water to the reaction system, by subjecting the alkane and ammonia in the gaseous state to catalytic oxidation in the presence of an oxide comprising molybdenum (Mo), vanadium (V), tellurium (Te), niobium (Nb) and certain types of metals, or an oxide comprising molybdenum (Mo), vanadium (V), tellurium (Te) and certain types of metals, as a complex oxide. The present invention has been attained on the basis of such a discovery.

Thus, the present invention provides a process for producing a nitrile, which comprises subjecting an alkane and ammonia in the gaseous state to catalytic oxidation in the presence of an oxide of the formula:

$$Mo_a V_b Te_c Nb_d X_x O_n \qquad (1)$$

wherein X is at least one element selected from the group consisting of Mg, Ca, Sr, Ba, Al, Ga, Tl, In, Ti, Zr, Hf, Ta, Cr, Mn, W, Fe, Ru, Co, Rh, Ni, Pd, Pt, Zn, Sn, Pb, As, Sb, Bi, La and Ce,
when $a=1$,
$b=0.01$ to $1.0$,
$c=0.01$ to $1.0$,
$d=0$ to $1.0$, and
$x=0.0005$ to $1.0$,
and n is a number such that the total valency of the metal elements is satisfied.

Now, the present invention will be described in detail with reference the preferred embodiments.

With respect to the oxide of the formula (1) to be used in the present invention, X is particularly preferably Mg, Ca,, Ba, Al, Ta, Cr, Mn, W, Fe, Co, Ni, Pd, Zn, Sn, Sb, Bi among the above elements. Further, it is preferred that in the formula (1), when $a=1$, $b=0.1$ to $0.6$, $c=0.05$ to $0.4$ and $x=0.05$ to $0.6$.

Such a complex oxide may be prepared by a following method.

For example, in the case of $Mo_a V_b Te_c Nb_d Sn_x O_n$, added sequentially to an aqueous solution containing predetermined amount of ammonium metavanadate, are an aqueous solution of tin oxalate, an aqueous solution of telluric acid, an aqueous solution of ammonium niobium oxalate and an aqueous solution of ammonium paramolybdate in such amounts that the atomic ratios of the respective metal elements would fall in the ranges specified above, and the mixture is evaporated to dryness at a temperature of from 100° to 200° C., and the dried product is calcined at a temperature of from 350° to 700° C. to obtain a desired complex oxide.

The materials for the complex oxide are not limited to the ones mentioned above. For example, $V_2O_5$, $V_2O_3$, $VOCl_3$ or $VCl_4$ may be used instead of ammonium metavanadate, and tin nitrate, tin acetate, $SnCl_2$, $SnCl_4$, SnO or $SnO_2$ may be used instead of the above-mentioned tin oxalate. Likewise, $TeO_2$ may be used instead of telluric acid; $NbCl_5$, $Nb_2O_5$ or niobic acid may be used instead of ammonium niobium oxalate; and $MoO_3$, $MoCl_5$, phosphomolybdic acid or silicomolybdic acid may be used instead of ammonium paramolybdate. Further, it is possible to use a heteropolyacid which contains mixed-coordinate molybdenum and vanadium, such as molybdovanadophosphoric acid.

Such a complex oxide may be used alone. However, it may be used together with a conventional carrier such as silica, alumina, titania, aluminosilicate or diatomaceous earth. Further, depending upon the scale or system of the reaction, it may be molded into a proper shape and particle size.

The process of the present invention is a process for producing a nitrile by subjecting an alkane to a gas phase catalytic oxidation reaction with ammonia in the presence of the above complex oxide.

In the present invention, the alkane as the starting material is not particularly limited and may, for example, be methane, ethane, propane, butane, isobutane, pentane, hexane, or heptane, or cyclohexane may be used. However, in view of the industrial application of nitriles to be produced, it is particularly preferred to employ a lower alkane having from 1 to 4 carbon atoms, particularly propane or isobutane.

The detailed mechanism of the oxidation reaction of the present invention is not clearly understood. However, the oxidation reaction is conducted by the oxygen atoms present in the above complex oxide or by the molecular oxygen present in the feed gas. When molecular oxygen is incorporated in the feed gas, the oxygen may be pure oxygen gas. However, since the purity is not required, it is usually economical to us an oxygen containing gas such as air. When no oxygen is incorporated in the feed gas, it is advisable to supply the alkane-ammonia gas mixture and the oxygen-containing gas alternately to prevent deterioration of the complex oxide by reduction, or to adopt a method wherein by means of a mobile bed type reactor, the complex oxide is continuously supplied to a oxidative regenerator so that it will be regenerated for reuse.

The present invention will be described in further detail with respect to a case where propane is used as the alkane and air is used as the oxygen source. The proportion of air to be supplied for the reaction is important with respect to the selectivity for the resulting acrylonitrile. Namely, high selectivity for acrylonitrile is obtained when air is supplied within a range of at most 25 mols, particularly from 1 to 15 mols per mol of propane. The proportion of ammonia to be supplied for the reaction is preferably within a range of from 0.2 to 5 mols, particularly from 0.5 to 3 mols, per mol of propane. This reaction may usually be conducted under atmospheric pressure, but may be conducted under a slightly increased pressure or a slightly reduced pressure.

The process of the present invention can be conducted at a temperature of e.g. from 380° to 480° C., which is lower than the temperature for conventional ammooxidation of alkanes. More preferably, the temperature is from 400° to 450° C. The gas space velocity SV in the gas phase reaction is usually within a range of from 100 to 10,000 hr$^{-1}$, preferably from 300 to 2,000 hr$^{-1}$. As a diluent gas for adjusting the space velocity and the oxygen partial pressure, an inert gas such as nitrogen, argon or helium can be employed. When ammooxidation of propane is conducted by the method of the present invention, in addition to acrylonitrile, carbon monooxide, carbon dioxide, acetonitrile, hydrocyanic acid, acrolein, etc. will form as by-products, but their amounts are very small.

Now, the present invention will be described in further detail with reference to Examples and Comparative Examples. However, it should be understood that the present invention is by no means restricted to such specific Examples.

In the following Examples and Comparative Examples, the conversion (%), the selectivity (%) and the yield (%) are shown by the following formulas, respectively:

$$\text{Conversion of alkane (\%)} = \frac{\text{mols of consumed alkane}}{\text{mols of supplied alkane}} \times 100$$

$$\text{Selectivity of objective nitrile (\%)} = \frac{\text{mols of objective nitrile obtained}}{\text{mols of consumed alkane}} \times 100$$

$$\text{Yield of objective nitrile (\%)} = \frac{\text{mols of supplied alkane}}{\text{mols of objective nitrile obtained}} \times 100$$

EXAMPLE 1

A complex oxide having an empirical formula $Mo_1V_{0.4}Te_{0.2}Nb_{0.1}Mn_{0.1}O_n$ was prepared as follows.

In 117 ml of warm water, 4.21 g of ammonium metavanadate was dissolved, and 4.13 g of telluric acid, 15.89 g of ammonium paramolybdate and 3.99 g of manganese acetate tetrahydrate were sequentially added thereto to obtain a uniform aqueous solution. Further, 3.99 g of ammonium niobium oxalate was dissolved in 17.9 ml of water and added thereto. The obtained aqueous solution was evaporated to dryness at about 150° C. to obtain a solid material.

This solid material was molded into a tablet of 5 mm in diameter and 3 mm in length by a tabletting machine, followed by pulverization and sieving to obtain a powder of from 16 to 28 mesh. The powder was calcined at a temperature of 350° C., and then used for the reaction.

0.5 ml of the complex oxide thus obtained, was charged into a reactor. Then, a gas phase catalytic reaction was conducted at a reaction temperature of 440° C. and at a space velocity SV of 1000 hr$^{-1}$ by supplying a feed gas in a molar ratio of propane:ammonia:air = 1:1.2:10. The results are shown in Table 1.

EXAMPLE 2

A complex oxide was prepared in the same manner as in Example 1 except that 2.24 g of nickel acetate tetrahydrate was used instead of manganese acetate tetrahydrate. The composition of the obtained complex oxide was $Mo_1V_{0.4}Te_{0.2}Nb_{0.1}Ni_{0.1}O_n$.

Further, a gas phase catalytic reaction was conducted by supplying propane, ammonia and air in the same manner as in Example 1 (reaction temperature: 440° C.). The results are shown in Table 1.

EXAMPLE 3

A complex oxide was prepared in the same manner as in Example 1 except that 1.34 g of magnesium oxalate dihydrate was used instead of manganese acetate tetrahydrate. The composition of the obtained complex oxide was $Mo_1V_{0.4}Te_{0.2}Nb_{0.1}Mg_{0.1}O_n$.

Further, a gas phase catalytic reaction was conducted by supplying propane, ammonia and air in the same manner as in Example 1 (reaction temperature: 450° C.). The results are shown in Table 1.

EXAMPLE 4

A complex oxide was prepared in the same manner as in Example 1 except that 3.85 g of ammonium iron oxalate trihydrate was used instead of manganese acetate tetrahydrate. The composition of the obtained complex oxide was $Mo_1V_{0.4}Te_{0.2}Nb_{0.1}Fe_{0.1}O_n$.

Further, a gas phase catalytic reaction was conducted by supplying propane,, ammonia and air in the same manner as in Example 1 (reaction temperature: 420° C.). The results are shown in Table 1.

EXAMPLE 5

A complex oxide was prepared in the same manner as in Example 1 except that 2.13 g of tin acetate tetrahydrate was used instead of manganese acetate tetrahydrate. The composition of the obtained complex oxide was $Mo_1V_{0.4}Te_{0.2}Nb_{0.1}Sn_{0.1}O_n$.

Further, a gas phase catalytic reaction was conducted by supplying propane, ammonia and air in the same manner as in Example 1 (reaction temperature:440° C., SV: 2000 hr$^{-1}$). The results are shown in Table 1.

EXAMPLE 6

A complex oxide was prepared in the same manner as in Example 1 except that 0.24 g of cobalt acetate tetrahydrate was used instead of manganese acetate tetrahydrate. The composition of the obtained complex oxide was $Mo_1V_{0.4}Te_{0.2}Nb_{0.1}Co_{0.1}O_n$.

Further, a gas phase catalytic reaction was conducted by supplying propane, ammonia and air in the same manner as in Example 1 (reaction temperature: 420° C., SV: 500 hr$^{-1}$) The results are shown in Table 1.

COMPARATIVE EXAMPLE 1

A complex oxide was prepared in the same manner as in Example 1 except that the niobium and manganese were not used. The composition of the obtained complex oxide was $Mo_1V_{0.4}Te_{0.2}O_n$.

Further, a gas phase catalytic reaction was conducted by supplying propane, ammonia and air in the same manner as in Example 1 (reaction temperature: 400° C., SV: 500 hr$^{-1}$ and 1000 hr$^{-1}$). The results are shown in Table 1.

COMPARATIVE EXAMPLE 2

A complex oxide was prepared in the same manner as in Example 1 except that the manganese component was not used. The composition of the obtained complex oxide was $Mo_1V_{0.4}Te_{0.2}Nb_{0.1}O_n$.

Further, a gas phase catalytic reaction was Conducted by supplying propane, ammonia and air in the same manner as in Example 1 (reaction temperature: 420° C., SV: 500 hr$^{-1}$, and reaction temperature: 440° C., SV: 1000 hr$^{-1}$). The results are shown in Table 1.

ferric oxalate were sequentially added thereto to obtain a uniform aqueous solution. This solution was heated and then evaporated to dryness at about 150° C. to obtain a solid material.

This solid material was molded into a tablet of 5 mm in diameter and 3 mm in length by a tabletting machine, followed by pulverization and sieving to obtain a powder of from 16 to 28 mesh. The powder was calcined at 350° C. for 3 hours under an air stream, and then used for the reaction.

0.5 ml of the complex oxide thus obtained, was charged into a reactor, and a gas phase catalytic reaction was conducted at a reaction temperature of 420° C. at a space velocity SV 500 hr$^{-1}$ by supplying a feed gas in a molar ratio of propane:ammonia:air=1:1.2:10. The results are shown in Table 2.

EXAMPLE 8

A complex oxide was prepared in the same manner as in Example 7 except that 1.28 g of magnesium nitrate hexahydrate was used instead of ammonium ferric oxalate. The empirical composition of the obtained complex oxide was $Mo_1V_{0.4}Te_{0.2}Mg_{0.1}O_n$.

Further, a gas phase catalytic reaction was conducted by supplying propane, ammonia and air in the same manner as in Example 1 (reaction temperature: 420° C.). The results are shown in Table 2.

EXAMPLE 9

A complex oxide was prepared in the same manner as in Example 7 except that 1.88 g of aluminum nitrate trihydrate was used instead of ammonium ferric oxalate. The empirical composition of the obtained complex oxide was $Mo_1V_{0.4}Te_{0.2}Al_{0.1}O_n$.

Further, a gas phase catalytic reaction was conducted by supplying propane, ammonia and air in the same manner as in Example 1 (reaction temperature: 420° C.). The results are shown in Table 2.

EXAMPLE 10

A complex oxide was prepared in the same manner as in Example 7 except that 1.18 g of calcium nitrate tetrahydrate was used instead of ammonium ferric oxalate. The empirical composition of the obtained complex oxide was $Mo_1V_{0.4}Te_{0.2}Ca_{0.1}O_n$.

TABLE 1

| | Complex oxide (atomic ratio) | SV (hr$^{-1}$) | Temp (°C.) | Conversion of propane (%) | Selectivity for acrylonitrile (%) | Yield of acrylonitrile (%) |
|---|---|---|---|---|---|---|
| Example 1 | $Mo_1V_{0.4}Te_{0.2}Nb_{0.1}Mn_{0.1}O_n$ | 1000 | 440 | 57.5 | 41.5 | 23.9 |
| Example 2 | $Mo_1V_{0.4}Te_{0.2}Nb_{0.1}Ni_{0.1}O_n$ | 1000 | 440 | 59.1 | 37.5 | 22.1 |
| Example 3 | $Mo_1V_{0.4}Te_{0.2}Nb_{0.1}Mg_{0.1}O_n$ | 1000 | 450 | 48.5 | 43.5 | 21.1 |
| Example 4 | $Mo_1V_{0.4}Te_{0.2}Nb_{0.1}Fe_{0.1}O_n$ | 1000 | 420 | 48.4 | 35.0 | 16.9 |
| Example 5 | $Mo_1V_{0.4}Te_{0.2}Nb_{0.1}Sn_{0.1}O_n$ | 2000 | 440 | 57.8 | 43.6 | 25.2 |
| Example 6 | $Mo_1V_{0.4}Te_{0.2}Nb_{0.1}Co_{0.1}O_n$ | 500 | 420 | 46.7 | 39.1 | 18.2 |
| Comparative Example 1 | $Mo_1V_{0.4}Te_{0.2}O_n$ | 500 | 400 | 14.5 | 24.1 | 3.5 |
| | $Mo_1V_{0.4}Te_{0.2}O_n$ | 1000 | 400 | 9.5 | 24.2 | 2.3 |
| Comparative Example 2 | $Mo_1V_{0.4}Te_{0.2}Nb_{0.1}O_n$ | 500 | 420 | 43.2 | 27.1 | 11.7 |
| | $Mo_1V_{0.4}Te_{0.2}Nb_{0.1}O_n$ | 1000 | 440 | 48.8 | 34.2 | 16.7 |

EXAMPLE 7

A complex oxide having the empirical formula $Mo_1V_{0.4}Te_{0.2}Fe_{0.1}O_n$ was prepared as follows.

In 65 ml of warm water, 2.34 g of ammonium metavanadate was dissolved, and 2.3 g of telluric acid, 8.83 g of ammonium paramolybdate and 2.14 g of ammonium Further, a gas phase catalytic reaction was conducted by supplying propane, ammonia and air in the same manner as in Example 1 (reaction temperature: 400° C.). The results are shown in Table 2.

EXAMPLE 11

A complex oxide was prepared in the same manner as in Example 7 except that 1.31 g of barium nitrate was used instead of ammonium ferric oxalate. The empirical composition of the obtained complex oxide was $Mo_1V_{0.4}Te_{0.2}Ba_{0.1}O_n$.

Further, a gas phase catalytic reaction was conducted by supplying propane, ammonia and air in the same manner as in Example 7 (reaction temperature: 400° C.). The results are shown in Table 2.

EXAMPLE 12

A complex oxide was prepared in the same manner as in Example 7 except that 0.87 g of antimony chlorooxide was used instead of ammonium ferric oxalate. The empirical composition of the obtained complex oxide was $Mo_1V_{0.4}Te_{0.2}Sb_{0.1}O_n$.

Further, a gas phase catalytic reaction was conducted by supplying propane,, ammonia and air in the same manner as in Example 7 (reaction temperature: 400° C.). The results are shown in Table 2.

EXAMPLE 13

A complex oxide was prepared in the same manner as in Example 8 except that 2.43 g of bismuth nitrate pentahydrate was used instead of ammonium ferric oxalate. The empirical composition of the obtained complex oxide was $Mo_1V_{0.4}Te_{0.2}Bi_{0.1}O_n$.

Further, a gas phase catalytic reaction was conducted by supplying propane, ammonia and air in the same manner as in Example 8 (reaction temperature: 400° C.). The results are shown in Table 2.

EXAMPLE 14

A complex oxide was prepared in the same manner as in Example 7 except that 1.49 g of zinc nitrate hexahydrate was used instead of ammonium ferric oxalate. The empirical composition of the obtained complex oxide was $Mo_1V_{0.4}Te_{0.2}Zn_{0.1}O_n$.

Further, a gas phase catalytic reaction was conducted by supplying propane, ammonia and air in the same manner as in Example 7 (reaction temperature: 420° C.). The results are shown in Table 2.

EXAMPLE 15 as in
A complex oxide was prepared in the same manner Example 7 except that 4.01 g of tantalum oxalate was used instead of ammonium ferric oxalate. The empirical composition of the obtained complex oxide was $Mo_1V_{0.4}Te_{0.2}Ta_{0.2}O_n$.

Further, a gas phase catalytic reaction was conducted by supplying propane, ammonia and air in the same manner as in Example 7 (reaction temperature: 420° C.). The results are shown in Table 2.

EXAMPLE 16

A complex oxide was prepared in the same manner as in Example 7 except that 2.32 g of ammonium metatungstate was used instead of ammonium ferric oxalate. The empirical composition of the obtained complex oxide was $Mo_1V_{0.4}Te_{0.2}W_{0.1}O_n$.

Further, a gas phase catalytic reaction was conducted by supplying propane, ammonia and air in the same manner as in Example 7 (reaction temperature: 400° C.). The results are shown in Table 2.

EXAMPLE 17

A complex oxide was prepared in the same manner as in Example 7 except that 1.44 g of manganese nitrate hexahydrate was used instead of ammonium ferric oxalate. The empirical composition of the obtained complex oxide was $Mo_1V_{0.4}Te_{0.2}Mn_{0.1}O_n$.

Further, a gas phase catalytic reaction was conducted by supplying propane, ammonia and air in the same manner as in Example 7 (reaction temperature: 400° C.). The results are shown in Table 2.

EXAMPLE 18

A complex oxide was prepared in the same manner as in Example 7 except that 1.46 g of cobalt nitrate hexahydrate was used instead of ammonium ferric oxalate. The empirical composition of the obtained complex oxide was $Mo_1V_{0.4}Te_{0.2}Co_{0.1}O_n$.

Further, a gas phase catalytic reaction was conducted by supplying propane, ammonia and air in the same manner as in Example 7 (reaction temperature: 420° C.). The results are shown in Table 2.

EXAMPLE 19

A complex oxide was prepared in the same manner as in Example 7 except that 1.45 g of nickel nitrate hexahydrate was used instead of ammonium ferric oxalate. The empirical composition of the obtained complex oxide was $Mo_1V_{0.4}Te_{0.2}Ni_{0.1}O_n$.

Further, a gas phase catalytic reaction was conducted by supplying propane, ammonia and air in the same manner as in Example 7 (reaction temperature: 420° C.). The results are shown in Table 2.

EXAMPLE 20

A complex oxide was prepared in the same manner as in Example 7 except that 2.00 g of chromium nitrate nonahydrate was used instead of ammonium ferric oxalate. The empirical composition of the obtained complex oxide was $Mo_1V_{0.4}Te_{0.2}Cr_{0.1}O_n$.

Further, a gas phase catalytic reaction was conducted by supplying propane, ammonia and air in the same manner as in Example 1 (,reaction temperature: 420° C.). The results are shown in Table 2.

COMPARATIVE EXAMPLE 3

A complex oxide was prepared in the same manner as in Example 7 except that no iron component was used. The empirical composition of the obtained complex oxide was $Mo_1V_{0.4}Te_{0.2}O_n$.

Further, a gas phase catalytic reaction was conducted by supplying propane, ammonia and air in the same manner as in Example 7. The results are shown in Table 2.

TABLE 2

|  | Complex oxide (atomic ratio) | Temp (°C.) | Conversion of propane (%) | Yield of acrylonitrile (%) |
|---|---|---|---|---|
| Example 7 | $Mo_1V_{0.4}Te_{0.2}Fe_{0.1}O_n$ | 420 | 52.2 | 16.0 |
| Example 8 | $Mo_1V_{0.4}Te_{0.2}Mg_{0.1}O_n$ | 420 | 53.5 | 18.1 |
| Example 9 | $Mo_1V_{0.4}Te_{0.2}Al_{0.1}O_n$ | 420 | 52.7 | 17.6 |
| Example 10 | $Mo_1V_{0.4}Te_{0.2}Ca_{0.1}O_n$ | 400 | 47.2 | 14.0 |
| Example 11 | $Mo_1V_{0.4}Te_{0.2}Ba_{0.1}O_n$ | 400 | 46.3 | 14.0 |
| Example 12 | $Mo_1V_{0.4}Te_{0.2}Sb_{0.1}O_n$ | 400 | 43.0 | 15.7 |
| Example 13 | $Mo_1V_{0.4}Te_{0.2}Bi_{0.1}O_n$ | 400 | 47.6 | 17.3 |
| Example 14 | $Mo_1V_{0.4}Te_{0.2}Zn_{0.1}O_n$ | 420 | 52.7 | 16.6 |
| Example 15 | $Mo_1V_{0.4}Te_{0.2}Ta_{0.1}O_n$ | 420 | 46.8 | 17.5 |
| Example 16 | $Mo_1V_{0.4}Te_{0.2}W_{0.1}O_n$ | 400 | 40.8 | 15.4 |

TABLE 2-continued

| | Complex oxide (atomic ratio) | Temp (°C.) | Conversion of propane (%) | Yield of acrylonitrile (%) |
|---|---|---|---|---|
| Example 17 | $Mo_1V_{0.4}Te_{0.2}Mn_{0.1}O_n$ | 400 | 50.2 | 15.9 |
| Example 18 | $Mo_1V_{0.4}Te_{0.2}Co_{0.1}O_n$ | 420 | 51.4 | 17.0 |
| Example 19 | $Mo_1V_{0.4}Te_{0.2}Ni_{0.1}O_n$ | 420 | 51.6 | 15.8 |
| Example 20 | $Mo_1V_{0.4}Te_{0.2}Cr_{0.1}O_n$ | 420 | 50.6 | 16.4 |
| Comparative Example 3 | $Mo_1V_{0.4}Te_{0.2}O_n$ | 420 | 14.5 | 3.5 |

EXAMPLES 21 TO 23

Using complex oxides prepared in the same manner as in Examples 7, 13 and 17, respectively, gas phase catalytic reactions of propane and ammonia were conducted. In each case, 0.5 ml of the complex oxide was charged into a reactor, and the gas phase catalytic reaction was conducted at a reaction temperature of 400° C. at a space velocity SV of 1000 hr$^{-1}$ by supplying a feed gas in a molar ratio of propane:ammonia:air=1:1.2:10. The results are shown in Table 3.

COMPARATIVE EXAMPLE 4

Using a composite oxide of the empirical composition $Mo_1V_{0.4}Te_{0.2}O_x$ prepared in the same manner as in Comparative Example 3, a gas phase catalytic reaction was conducted under the same conditions as in Example 21. The results are shown in Table 3.

TABLE 3

| | Complex oxide (atomic ratio) | Conversion of propane (%) | Yield of acrylonitrile (%) |
|---|---|---|---|
| Example 21 | $Mo_1V_{0.4}Te_{0.2}Fe_{0.1}O_n$ | 43.6 | 15.1 |
| Example 22 | $Mo_1V_{0.4}Te_{0.2}Bi_{0.1}O_n$ | 43.6 | 16.6 |
| Example 23 | $Mo_1V_{0.4}Te_{0.2}Mn_{0.1}O_n$ | 42.2 | 15.4 |
| Comparative Example 4 | $Mo_1V_{0.4}Te_{0.2}O_n$ | 9.5 | 2.3 |

EXAMPLE 24

0.2 cc of the oxide obtained in Example 7 was charged into a reactor, and a gas phase catalytic reaction was conducted at a reaction temperature of 440° C. at a space velocity of 2000 hr$^{-1}$ by supplying a reaction gas in a molar ratio of propane:ammonia:nitrogen=10:1.6:11.2 for 3 minutes, i.e. in the absence of oxygen. The results are shown in Table 4.

EXAMPLE 25

A complex oxide was prepared in the same manner as in Example 7 except that 24.86 g of ammonium titanium oxalate was used instead of ammonium ferric oxalate. The composition of the obtained complex oxide was $Mo_1V_{0.4}Te_{0.2}Ti_{0.4}O_n$.

Further, a gas phase catalytic reaction was conducted by supplying propane, ammonia and nitrogen in the same manner as in Example 24. The results are shown in Table 4.

EXAMPLE 26

A complex oxide was prepared in the same manner as in Example 7 except that 0.593 g of stannic oxalate was used instead of ammonium ferric oxalate. The composition of the obtained complex oxide was $Mo_1V_{0.4}Te_{0.2}Sn_{0.1}O_n$.

Further, a gas phase catalytic reaction was conducted by supplying propane, ammonia and nitrogen in the same manner as in Example 24. The results are shown in Table 4.

EXAMPLE 27

Using a complex oxide prepared in the same manner as in Example 9, a gas phase catalytic reaction was conducted by supplying propane, ammonia and nitrogen in the same manner as in Example 24. The results are shown in Table 4.

COMPARATIVE EXAMPLE 5

Using a complex oxide having the empirical composition $Mo_1V_{0.4}Te_{0.2}O_x$ prepared in the same manner as in Comparative Example 3, a gas phase catalytic reaction was conducted by supplying propane, ammonia and nitrogen in the same manner as in Example 24. The results are shown in Table 4.

TABLE 4

| | Complex oxide (atomic ratio) | Conversion of propane (%) | Yield of acrylonitrile (%) |
|---|---|---|---|
| Example 24 | $Mo_1V_{0.4}Te_{0.2}Fe_{0.1}O_n$ | 12.5 | 5.3 |
| Example 25 | $Mo_1V_{0.4}Te_{0.2}Ti_{0.1}O_n$ | 9.4 | 4.5 |
| Example 26 | $Mo_1V_{0.4}Te_{0.2}Sn_{0.1}O_n$ | 11.7 | 5.7 |
| Example 27 | $Mo_1V_{0.4}Te_{0.2}Al_{0.1}O_n$ | 12.3 | 5.6 |
| Comparative Example 5 | $Mo_1V_{0.4}Te_{0.2}O_n$ | 9.4 | 4.0 |

EXAMPLE 28

A complex oxide having the empirical composition $Mo_1V_{0.4}Te_{0.2}Nb_{0.1}Pd_{0.0008}O_n$ was prepared as follows.

In 117 ml of warm water, 4.21 g of ammonium metabanadate was dissolved, and 4.54 g of telluric acid, 15.89 g of ammonium paramolybdate and 1.4 ml of an aqueous palladium nitrate solution (concentration of Pd: 5.32 g/l) were sequentially added thereto to obtain a uniform aqueous solution. Further, 3.99 g of ammonium niobium oxalate was dissolved in 17.9 ml of water and added thereto. The aqueous solution thereby obtained was evaporated to dryness at about 150° C. to obtain a solid material.

This solid material was molded into a tablet of 5 mm in diameter and 3 mm in length by a tabletting machine, following pulverization and sieving to obtain a powder of from 16 to 28 mesh. The powder was calcined at a temperature of at least 350° C., and then used for the reaction.

0.5 ml of the complex oxide thus obtained, was charged into reactor, and a gas phase catalytic reaction was conducted at a reaction temperature of 440° C. at a space velocity SV of 2000 hr$^{-1}$ by supplying a feed gas at a molar ratio of propane:ammonia:air=1:1.2:10. As a result, the conversion of propane was 62.2%, the selectivity for acrylonitrile was 51.9%, and the yield of acrylonitrile was 32.3%.

According to the process of the present invention, by using a novel complex oxide while an alkane is used as the starting material, a desired nitrile can be produced in good yield at a relatively low temperature at a level of from 380° to 480° C. without requiring the presence of a halide or water in the reaction system.

We claim:

1. A process for producing a nitrile, which comprises subjecting an alkane having 3-4 carbon atoms, a molecular oxygen containing gas, and ammonia in the gaseous state to catalytic oxidation at a temperature of from 380° to 480° C. in the presence of an oxide of the formula:

$$Mo_a V_b Te_c Nb_d X_x O_n \qquad (1)$$

wherein X is at least one element selected from the group consisting of Mg, Ca, Sr, Ba, Al, Ga, Tl, In, Ti, Zr, Hf, Ta, Cr, Mn, W, Fe, Ru, Co, Rh, Ni, Pd, Pt, Zn, Sn, Pb, As, Sb, Bi, La and Ce, when a=1,
b=0.01 to 1.0,
c=0.01 to 1.0,
d=0 to 1.0, and
x=0.0005 to 1.0, and n is a number such that the total valency of the metal elements is satisfied.

2. The process according to claim 1, wherein in the formula (1), when a=1, b=0.1 to 0.6, c=0.05 to 0.4 and x=0.005 to 0.6.

3. The process according to claim 1, wherein the alkane is propane or isobutane.

4. The process according to claim 1, wherein the alkane is propane.

5. The process according to claim 1, wherein the ammonia is present in an amount of from 0.2 to 5 mols per mol of the alkane.

6. The process according to claim 1, which is carried out at a temperature of from 4000° to 450° C.

7. The process according to claim 1, where d=0.

8. A process for producing acrylonitrile or methacrylonitrile, which process comprises subjecting propane or isobutane, a molecular oxygen containing gas and ammonia in the gaseous state to catalytic oxidation at a temperature of from 400° to 450° in the presence of an oxide of the formula:

$$Mo_a V_b Te_c Nb_d X_x O_n \qquad (1)$$

wherein X is at least one element selected from the group consisting of Mg, Ca, sr, Ba, Al, Ga, Tl, In, Ti, Zr, Hf, Ta, Cr, Mn, W, Fe, Ru, Co, Rh, Ni, Pd, Pt, Zn, Sn, Pb, As, Sb, Bi, La, Ce, when a=1,
b=about 0.4,
c=about 0.2,
d=0 or about 0.1
x=about 0.1 or about 0.0008 and n is a number such that the total valency of the metal elements is satisfied.

9. The process according to claim 8, wherein the alkane is propane.

10. The process according to claim 8, wherein the ammonia is present in an amount of from 0.2 to 5 mols per mol of the alkane.

11. The process according to claim 8, wherein d=0.

* * * * *